United States Patent
Shany et al.

(10) Patent No.: US 9,168,028 B2
(45) Date of Patent: *Oct. 27, 2015

(54) CARTRIDGE FOR A BIOLOGICAL SAMPLE

(75) Inventors: Vered Shany, Ramat-Gan (IL); Isaac Tavori, Ramat-Gan (IL)

(73) Assignee: LOTUS BIO (NYMPHAEA) LTD, Ramat-Gan (IL)

( * ) Notice: Subject to any disclaimer, the term of this patent is extended or adjusted under 35 U.S.C. 154(b) by 727 days.

This patent is subject to a terminal disclaimer.

(21) Appl. No.: 12/739,337

(22) PCT Filed: Oct. 23, 2008

(86) PCT No.: PCT/IB2008/054381
§ 371 (c)(1),
(2), (4) Date: Dec. 21, 2010

(87) PCT Pub. No.: WO2009/053927
PCT Pub. Date: Apr. 30, 2009

(65) Prior Publication Data
US 2011/0086378 A1    Apr. 14, 2011

Related U.S. Application Data

(60) Provisional application No. 60/981,856, filed on Oct. 23, 2007.

(51) Int. Cl.
G01N 31/22    (2006.01)
A61B 10/00    (2006.01)
B01L 3/00     (2006.01)
B01L 7/00     (2006.01)

(52) U.S. Cl.
CPC ........ *A61B 10/0045* (2013.01); *B01L 3/502715* (2013.01); *B01L 3/502753* (2013.01); *B01L 7/52* (2013.01); *B01L 2200/027* (2013.01); *B01L 2300/0681* (2013.01); *B01L 2300/0864* (2013.01); *B01L 2400/0481* (2013.01); *B01L 2400/0487* (2013.01)

(58) Field of Classification Search
CPC .......................... A61B 10/0045; B01L 3/502
See application file for complete search history.

(56) References Cited

U.S. PATENT DOCUMENTS

| 5,296,375 A | 3/1994 | Kricka et al. | |
| 5,686,302 A * | 11/1997 | Zech | 435/305.2 |
| 7,022,517 B1 | 4/2006 | McDevitt et al. | |
| 2003/0119050 A1 * | 6/2003 | Shai | 435/6 |
| 2006/0257993 A1 | 11/2006 | McDevitt et al. | |

OTHER PUBLICATIONS

International Search Report dated Apr. 9, 2009 in corresponding International Application No. PCT/IB2008/054381.

* cited by examiner

Primary Examiner — Jyoti Nagpaul

(57) ABSTRACT

An assay device comprising a compartment adapted to receive a sealed removable cartridge, wherein said cartridge is adapted to contain a biologic sample and internally comprises two or more assay locations, wherein said cartridge is adapted to facilitate two or more assays of said biologic sample; and an actuator adapted to interface with said cartridge to transport said biologic sample towards at least one of said assay locations.

25 Claims, 8 Drawing Sheets

CARTRIDGE FOR A BIOLOGICAL SAMPLE

CROSS-REFERENCE TO RELATED APPLICATIONS

This application is a national stage of International Application No. PCT/IB2008/054381 filed Oct. 23, 2008 and claims the benefit of U.S. Provisional Patent Application 60/981,856 filed on Oct. 23, 2007, which is incorporated herein by reference.

FIELD OF THE DISCLOSURE

Embodiments of the disclosure relate to a biologic sample assay device.

BACKGROUND

When diagnosing a sample, it is often required to reach a significant conclusion with respect to the sample's contents. Biological samples, such as semen, vaginal secretions, vaginal cells, blood, urine, saliva, lymph and the like, are commonly tested at the field, with portable apparatuses, tools or disposable diagnostics, or in laboratories. Laboratory work, including field work, often requires taking a portion of the sample, processing it in various ways using laboratory operations and finally assessing a result. Laboratory medicine commonly includes anatomic pathology histopathology, cytopathology, microscopy, clinical microbiology, bacteriology, virology, parasitology, immunology, mycology, clinical biochemistry instrumental analysis, enzymology, toxicology, endocrinology and hematology.

Over the past years, automated analyzers became more and more common in laboratories. An automated analyzer is often defined as a medical laboratory instrument designed to rapidly measure different chemicals and other characteristics in a samples, with minimal human assistance. The automation of laboratory testing does not usually remove the need for human expertise (as some results must still be evaluated by medical technologists and other qualified clinical laboratory professionals, and sometimes manual processing is required), but it does ease concerns about error reduction, staffing concerns and safety.

Applicant's U.S. Provisional Patent Application No. 60/981,856, filed Oct. 23, 2007, discloses a diagnostic device. This application is incorporated herein by reference in its entirety.

SUMMARY

There is provided, according to an embodiment, an assay device which includes a compartment adapted to receive a sealed removable cartridge, wherein the cartridge is adapted to contain a biologic sample and internally comprises two or more assay locations, wherein the cartridge is adapted to facilitate two or more assays of the biologic sample and an actuator adapted to interface with the cartridge to transport the biologic sample towards at least one of the assay locations.

According to further embodiments, the biologic sample may be selected from a group that includes a semen sample, a vaginal secretion sample, a vaginal cell sample, a blood sample, a urine sample, a saliva sample, a lymph sample, or any combination thereof.

According to additional embodiments, the two or more assays may be selected from a group that includes a sperm concentration assay, a semen pH assay, a leukocyte threshold assay, a sperm motility assay, a sperm morphology assay, a semen volume assay, a viscosity assay, a turbidity assay or any combination thereof. According to yet further embodiments, at least one of the assays may be adapted to facilitate diagnosis of at least one sexually transmitted disease (STD) selected from a group that includes: syphilis, gonorrhea, candida, human papilloma virus (HPV), mycoplasma, ureaplasma, human immunodeficiency virus (HIV), Chlamydia, herpes simplex virus, Hepatitis B, Trichomonas and Hepatitis C, or any combination thereof.

According to further embodiments, the housing of said cartridge may be substantially rigid. The housing of the cartridge may be substantially flexible.

According to yet additional embodiments, the assay device may further include at least one sensor adapted to interface with the cartridge to facilitate at least one assay of the assays. The actuator of the assay device may include a pump.

According to additional embodiments, the assay device may further include a computerized control adapted to perform at least one action selected from a group consisting of: facilitate at least one of the assays, receive a reading from the at least one sensor, compute a result of at least one of the assays, compute a combined measure of results of two or more of the assays and compute a predicted optimal fertilization date.

According to further embodiments, the cartridge may further include a cell separation system, which includes a first chamber adapted to contain at least a portion of the semen sample; and a second chamber adapted to receive motile cells upon introduction of a separation-enabling agent into the first chamber. The cell separation system may be adapted to assess motility of sperm cells. The cell separation system may be adapted to isolate motile sperm of said semen sample for a usage selected from a group consisting of: intra uterine insemination (IUI), vaginal insemination, and in-vitro fertilization (IVF).

According to yet further embodiments, the cartridge may be further adapted to manipulate the biologic sample using at least one manipulation technique selected from a group which includes homogenization, liquefaction, deposition on a reagent-loaded pad, mixing with a reagent, deposition on an antibody-loaded pad, incubation, separation, migration, sedimentation, or any combination thereof.

According to some embodiments there is provided a method for operating an assay device, the method includes: inserting a sealed removable cartridge into a compartment of the assay device; inserting a biologic sample into the cartridge; and activating the assay device to facilitate, within the cartridge, two or more assays of the biologic sample.

According to further embodiments, the method for operating an assay device may further include operating an actuator of the assay device for interfacing with the cartridge and for transporting the biologic sample towards at least two assay locations where the two or more assays are facilitated.

According to yet further embodiments, the biologic sample in the method for operating an assay device may be selected from a group that includes a semen sample, a vaginal secretion sample, a vaginal cell sample, a blood sample, a urine sample, a saliva sample, a lymph sample, or any combination thereof.

According to additional embodiments, the two or more assays in the method for operating an assay device may be selected from a group that include a sperm concentration assay, a semen pH assay, a leukocyte threshold assay, a sperm motility assay, a sperm morphology assay, a semen volume assay, or any combination thereof. According to additional embodiments, at least one of the assays is adapted to facilitate diagnosis of at least one STD selected from a group that includes syphilis, gonorrhea, candida, HPV, mycoplasma, ureaplasma, HIV, Chlamydia, herpes simplex virus, Hepatitis B, Trichomonas, Hepatitis C, or any combination thereof.

According to additional embodiments, the method for operating an assay device may further include operating a computerized control for performing at least one action selected from a group consisting of: facilitate at least one of said assays, receive a reading from said at least one sensor, compute a result of at least one of said assays, compute a combined measure of results of two or more of said assays and compute a predicted optimal fertilization date.

According to yet further embodiments, the method for operating an assay device may further include operating a cell separation system of the cartridge, the operating includes: depositing at least a portion of the semen sample in a first chamber of the cell separation system; introducing a separation-enabling agent into the first chamber, to facilitate swimming of motile cell into a second chamber of the cell separation system. The method may further include collecting the motile cells from the second chamber. The collecting of the motile cells may include collecting of motile sperm, for a usage selected from a group that includes intra uterine insemination (IUI), vaginal insemination, in-vitro fertilization (IVF), or any combination thereof. The method may further include assessing motility of cells based on a relative amount of motile cells in the second chamber.

According to some embodiments, there is provided an assay device which includes a compartment adapted to receive a receptacle containing a reproductive system sample; one or more assay locations adapted to facilitate at least one assay of said reproductive system sample; and a result indicator adapted to indicate a result of said at least one assay.

According to further embodiments, the reproductive system sample includes a semen sample. The reproductive system sample includes a vaginal secretion According to additional embodiments, the assay device may further include an extraction mechanism adapted to extract at least a portion of the reproductive system sample from the receptacle. The extraction mechanism may include a strike handle. The extraction mechanism may include a peristaltic pump.

According to additional embodiments, the result indicator of the assay device may include a color-changeable pad.

According to yet further embodiments, the receptacle may include a condom.

According to additional embodiments, at least one of the assay locations may include a replaceable assay location adapted to be replaced by an additional assay location for facilitating an additional assay. The one or more assay locations may include two or more assay locations. The at least one assay may include two or more assays. The at least one assay may be selected from a group that includes a sperm concentration assay, a semen pH assay, a leukocyte threshold assay, a sperm motility assay, a sperm morphology assay, a semen volume assay, or any combination thereof. The at least one assay may be adapted to facilitate diagnosis of at least one STD selected from a group that includes syphilis, gonorrhea, candida, HPV, mycoplasma, ureaplasma, HIV, Chlamydia, herpes simplex virus, Hepatitis B, Trichomonas, Hepatitis C, or any combination thereof.

According to further embodiments, the assay location may further be adapted to manipulate the biologic sample using at least one manipulation technique selected from a group that includes: homogenization, liquefaction, deposition on a reagent-loaded pad, mixing with a reagent, deposition on an antibody-loaded pad, incubation, separation, migration, sedimentation, or any combination thereof.

In some embodiments, the assay device may further include a volume measurement chamber.

According to some embodiments there is provided a method for operating an assay device, the method includes: inserting a receptacle containing a reproductive system sample into a compartment of the assay device; extracting at least a portion of the reproductive system sample from the receptacle towards one or more assay locations, to facilitate at least one assay of the reproductive system sample; and reading at least one result of the at least one assay from a result indicator of the assay device.

According to some embodiments, the reproductive system sample may include a semen sample. The reproductive system sample may include a vaginal secretion sample.

According to further embodiments, the method may further include measuring a volume of the reproductive system sample.

According to additional embodiments, the biologic sample is selected from a group that includes a semen sample, a vaginal secretion sample, a vaginal cell sample, a blood sample, a urine sample, a saliva sample, a lymph sample, or any combination thereof.

According to yet further embodiments, the at least one assay in the method may be selected from a group that includes a sperm concentration assay, a semen pH assay, a leukocyte threshold assay, a sperm motility assay, a sperm morphology assay, a semen volume assay, or any combination thereof.

According to additional embodiments, the at least one assay may be adapted to facilitate diagnosis of at least STD selected from a group that includes: syphilis, gonorrhea, candida, HPV, mycoplasma, ureaplasma, HIV, Chlamydia, herpes simplex virus, Hepatitis B, Trichomonas, Hepatitis C, or any combination thereof.

According to further embodiments the method may further include replacing at least one of the assay locations with an additional assay location.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

Figure 1A:
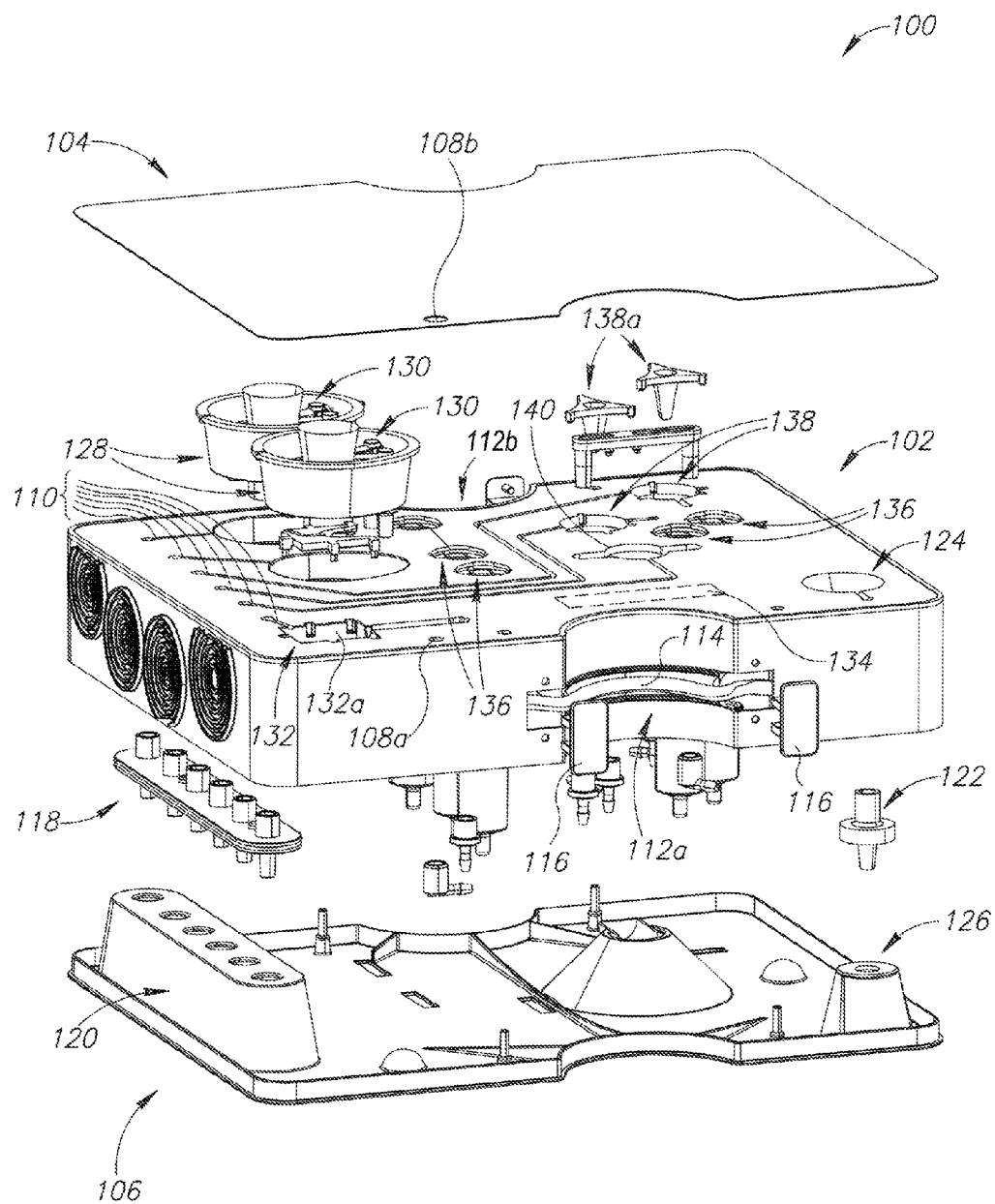
FIG. 1A shows an exploded view of a sealed, removable cartridge.

An aspect of some embodiments related to an assay device adapted to receive a sealed, removable cartridge containing a biologic sample. The assay device, in conjunction with the cartridge, may be used for assessing, by way of at least one assay, one or more parameters pertaining to the biologic sample. Additionally or alternatively, the assay device may be used for treating the biologic sample, such as, in the case of a semen sample, preparing it for intra uterine insemination (IUI), vaginal insemination, and/or in-vitro fertilization (IVF).

The biologic sample may be, for example, a semen sample, a vaginal secretion sample, a biologic cell sample, cervical mucus, a blood sample, a urine sample, a saliva sample, a lymph sample, or any other sample of biologic matter collected from a human or any other animal.

The cartridge may be substantially sealed, so that its biologic contents do not come in direct contact with the assay device and therefore no substantial contamination of the assay device and/or its immediate surroundings is caused. The sealed cartridge may, however, include an input port through which the biologic sample is fed, and/or an exhaust for discarding excess pressure—but both features may be configured in such a way that no substantial contamination is caused The assay device may interface with the cartridge using an actuator adapted to transport the biologic sample within the cartridge, towards one or more locations within the cartridge referred to as assay port(s) and/or treatment port(s), where the biologic sample is assessed and/or treated, respectively.

After use, the cartridge may be removed from the assay device and discarded. Alternatively, the cartridge may be stored (such as in cooled or cryogenic storage), along with its contents, for future testing, analysis and/or treatment of the sample. The cartridge may be configured such that only a part of it, containing portion of sample or the treated sample, is removed and stored for further testing, analysis and/or treatment.

The assay device may be relatively easy to operate and its operation may require no special laboratory training, so that a nurse, a physician, or any other caregiver may operates it in what is often referred to as a "point of care—a clinic, a medical institution or the like. Furthermore, the assay device may still be operated at the field, such as with portable apparatuses, tools or disposable diagnostics or in a laboratory.

Another aspect of some embodiments relates to an assay device adapted to receive a receptacle, such as a condom or any sample collection cup, containing a reproductive system sample such as semen, a vaginal secretion, any type of cell found in the vagina, cervical mucus and/or the like. In case the sample is semen, the assay device may be used for assessing, using at least one assay, one or more parameters pertaining to the semen sample and/or for treating the sperm sample.

The assay device may include an extraction mechanism for extracting the semen sample from the receptacle and for transporting the semen sample towards one or more assay locations where the semen sample is assessed.

The assay device may further include a result indicator, such as a color-changeable pad, for conveying the assessment results to its user.

Optionally, the user is the reproductive system sample provider, and, accordingly, the assay device may be adapted for use by a non-medically trained person. The assay device may be therefore offered to consumers either as a prescription medical device or as an over-the-counter (OTC) non-prescription device.

An additional aspect of some embodiments relates to the sealed, removable cartridge itself, which may be adapted for use in conjunction with an assay device or as a standalone solution.

The cartridge may be essentially rigid or essentially flexible, and may include an actuator interface for interfacing with an external means of pressure creation, so as to transport the biologic sample towards one or more assay and/or treatment ports. In case the cartridge is used with the assay device, the means of pressure difference creation may be a part of the assay device. Additionally or alternatively, the actuator may be an essentially flexible area of the cartridge, which may be pressed, optionally manually, to transport the sample.

A further aspect of some embodiments relates to a cell separation system. When used with sperm cells, it is adapted to assess motility of sperm cells and/or to isolate motile sperm cells of the semen sample for intra uterine insemination (IUI), vaginal insemination, or in-vitro fertilization (IVF) purposes. The cell separation system may also be used for separating other types of motile cells from immotile cells.

The cell separation system may include a first chamber adapted to contain at least a portion of a semen sample, and a second chamber adapted to receive motile cells upon introduction of a separation-enabling agent into the first chamber. The separation-enabling agent may be a gas, a liquid, a gel and/or any other suitable substance. After the separation, the first chamber may include an enriched population of immotile cells while the second chamber may include an enriched population of motile cells.

The cell separation system is optionally enclosed within the cartridge which is, in turn, adapted for insertion into the assay device. Alternatively, the cell separation system may be used as a standalone device, separate from the cartridge and assay device discussed above.

A Cartridge

Reference is now made to FIG. 1A, which shows an exploded view of an exemplary sealed, removable cartridge 100 (hereinafter "cartridge"), in accordance with an embodiment. Cartridge 100 may include a main body 102, a top cover 104 and optionally a base 106. Main body 102 is also shown, from a perspective view, in FIG. 1B. Main body 102 may be shaped as a rectangular box, a cylinder a flexible pouch and/or the like.

At least one of main body 102, top cover 104 and base 106 (the at least one of them may be jointly referred to as a "housing") may be essentially rigid, optionally made of a rigid material such as a polymer, a metal, glass or the like; alternatively, the at least one of main body 102, top cover 104 and/or base 106 may be made of a combination of rigid materials or of a combination of at least one rigid material and at least one flexible material.

Main body 102 may include an inlet 108*a* for insertion of a biologic sample into cartridge 100. A matching hole 108*b* may exist in top cover 104, to allow for a connection of a sample cup (not shown) to cartridge 100. The sample cup may have a tip adapted to be inserted, at least partially, into hole 108*b* and into inlet 108*a*, for supplying the biologic sample, while maintaining overall sealing as discussed above.

The inserted biologic sample may be transported inside cartridge 100 by virtue of at least one vacuum conduit, such as conduits 110. Conduits 110 may include internal tubing not visible in this figure. Conduits 110, when containing fluid, may be in contact with at least one actuator interface, such as actuator interfaces 112*a-b*. Actuator interfaces 112*a-b* may be shaped as a niche (optionally arched) in main body 102.

At least one external actuator (not shown) interfacing with actuator interfaces 112*a-b*, may provide conduits 110 with positive or negative gas pressure, so that the biologic sample is pushed or pulled along the conduits. For example, the actuator may be a peristaltic pump adapted to apply peristaltic pressure on a flexible pipe 114 which is in fluid contact with conduits 110. Flexible pipe 114 may be secured in place using, for example, two holders 116. Since there is optionally no fluid contact with the outside environment, by virtue of the peristaltic pump which operates externally on flexible pipe 114, the interfacing with the actuator does not cause contamination of the environment outside cartridge 100. For this purpose, any positive displacement system such as a syringe or a micropipette may be used. In some cases, electromagnetic fields may induce transportation of the sample or part of the sample using, for example, electrophoresis. In some cases, an electron enriched material such as a salt gradient may be used.

Alternatively or additionally, another actuator interface (not shown) may be an essentially flexible portion of cartridge 100 and/or its internal tubes, adapted for manual squeezing in order to transport the biologic sample.

A set of filters 118 may be positioned in between the edge of conduits 110 and an elevation 120 of base 106. Similarly, a filter 122 may be positioned in between a volume compartment 124 and another elevation 126 of base 106. Filters 122 and 118 may, by virtue of a suitably small pore size, provide ventilation to cartridge 100, while preventing leakage of hazardous materials to the environment.

Cartridge 100 may include two or more assay locations adapted to facilitate, within the cartridge, two or more assays of the biologic sample. The term "assay location", as referred to herein, may refer to any site within cartridge 100 adapted to act on the biologic sample and/or to analyze (or enable analysis by an external sensor of an assay device) at least one parameter pertaining to the sample.

For example, optionally when the sample is semen, the two or more assay locations may be selected from the following: at least one result pad such as two result pads 128; at least one pH and/or leukocytes test 132; at least one morphology assay 134; at least one reagent location, such as five reagent locations 136; at least one homogenizer, such as two homogenizers 138; at least one cell separation system 140; and at least one free volume compartment 124.

The assay location may be adapted to perform assays such as: Acrosom reaction assay, with or without calcium ionophore; a 23187 ARIC test and progesterone; bio active recombinant human ZP3 or active synthetic ZP3 peptides or analogues; adding reagent (for example 7-amino-actinomycin-D) to identify necrotic cells (SYTO 16) and reading results at 610 nm to 670 nm hence detecting apoptosis; Sanger sequencing; microplate assay; Polymerase Chain Reaction (PCR); probe-based hybridization assay; Processor Aided Motility count (CASA); Peroxidase; Zinc at 560 nm; Fructose at 470 nm; glucosidase at 405 nm; heavy metals assay; hormones such as Progesterone, Testosterone, and Estrogen; Antigen and/or cancer markers such as PSA, trace elements, carbohydrates proteoglycans or glycoproteins, minerals blood cells, plasma sexually transmitted disease (STD) assay (such as bacteria; yeast; Candida; virus) germs; Hidukes; Cervix carcinoma assay; PAP smear, blood assay; saliva assay; urine stick assay; Immunobead assay; mixed antiglobuline reaction test (MAR test) assay; induced acrosom reaction assay; measurement of reacting oxygen assay; ROS-Oxidative stress, anti oxidants, sperm-cervical mucus interaction assay, turbidity, viscosity and/or the like in ways known in the prior art.

The assay location may perform its assay at least partially by manipulating the biologic sample. By way of example, the assay location may utilize one or more of the following sample manipulation techniques: homogenization, liquefaction, mixing with a reagent, mixing with an antibody, deposition on a reagent-loaded pad, deposition on an antibody-loaded pad, concentration assessment, incubation, separation, migration, sedimentation viscosity assessment, turbidity, and the like.

The assay may be adapted to facilitate diagnosis of at least one STD. For example, syphilis, gonorrhea, candida, human papilloma virus (HPV), mycoplasma, ureaplasma, human immunodeficiency virus (HIV), Chlamydia, herpes simplex virus, Hepatitis B, Trichomonas, Hepatitis C and/or any other STD or infection.

The assay may further be adapted to facilitate diagnosis of one or more fertility factors or indicators of the tested subject, such as sperm cell concentration, semen volume, sperm cell morphology, semen pH, female secretion, sperm-cervical mucus interaction and/or the like Result pads 128 may be loaded with a reagent, and when sample is delivered via tips 130, reaction occurs and a result is shown (also referred to as classical flow-through diagnostics). Result pad 128 may be used as a strainer of the sample if reaction with reagents is performed within the homogenizer, as described below. Result pad 128 may be coupled with an antibody agent. When the sample is delivered via tips 130, it flows on or within result pads 128 until in reaction with an antibody compound (also referred to as classical lateral flow diagnostics). For example, anti CD 59 Result pad 128 may be operable for adding a reagent to the sample already on the result pad, using a gas and/or a liquid. The gas and/or the liquid may flow onto the sample through tips 130. Results may be read visually as color, a texture, a shape and/or the like. Results may also be read by a sensor.

Homogenizers 138 may be operable for homogenizing the sample prior to performing further assays and/or for mixing the sample with other reagents and/or biological components. Homogenization may be achieved via rapid movement of the sample, such as by mixing it using a rotateable or a reciprocating member. For example, triangular mixers 138a may be used for mixing the sample.

Semen pH threshold and leukocytes threshold tests 132 may include an absorbent pad holder 132a. The pad may include a color-changeable reagent indicating pH level, and/or a color-changeable reagent indicating leukocyte level. Such pads are available from different manufacturers.

Sperm cell morphology assay 134, which is shown only schematically since it is located within main body 102, may be adapted to hold, mark, stain and/or analyze morphological characteristics of the biologic sample. For example, if the biologic sample is semen, morphology assay 134 may analyze morphological defects of the sperm cells which may degrade its fertilization potential. Sperm cells morphology assay 134 may be detached from cartridge 100 and held for further diagnosis.

Reagent locations 136 may each include a reagent container. The reagent, upon contact with the biologic sample, may yield a reaction and/or a colored compound indicating existence and/or concentration of a component in the sample. Other reagents such as cell support medium, labeling compounds, markers, peptide and the like, available from various companies, may also be used.

Cell separation system 140 may be adapted to assess motility of sperm cells or any other cells of the biologic sample. Additionally or alternatively, cell separation system 140 may be adapted to isolate motile sperm cells of the semen sample for intra uterine insemination (IUI), vaginal insemination, and/or in-vitro fertilization (IVF) purposes.

Cell separation system 140 may be based upon the principle that motile cells (such as, for example, sperm cells) have swimming abilities, whereas immotile cells lack these abilities, at least to some extent. Therefore, cell separation system 140 is constructed such that motile cells move, essentially using their own swimming capabilities, to a different location, while a sediment of immotile cells is left behind.

Figure 3A:
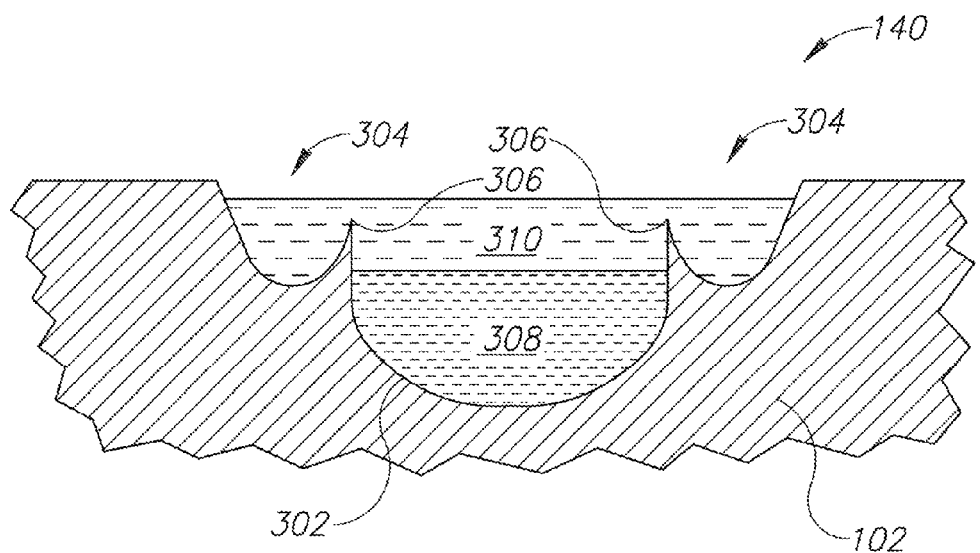
FIG. 3A shows a cross-sectional view of a cell separation system.
Figure 3B:
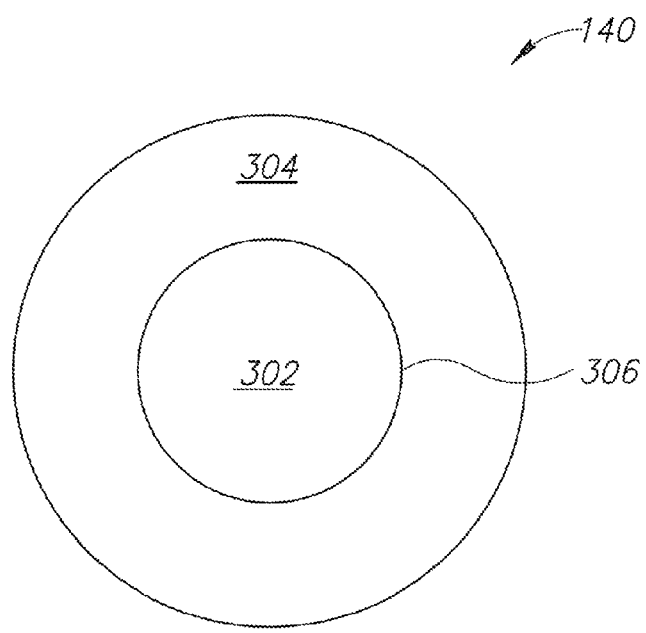
FIG. 3B shows a top view of a cell separation system.

Reference is now made to FIGS. 3A and 3B, which show cell separation system 140 in more detail. FIG. 3A is a cross-sectional view and FIG. 3B is a top view. Cells separation system 140 may include two chambers: a central chamber 302 shaped as a dimple in main body 102, and a peripheral chamber 304 shaped as a shallower, circumferential depression around the central chamber.

In order to operate cell separation system 140, a biologic sample (such as semen) 308 is deposited inside central chamber 302, while keeping the sample's level below a rim 306. Rim 306, may be dimensioned and designed with specific surface roughness or serration in order to facilitate required surface tension capabilities for specific sample/reagent combination. A separation-enabling agent 310, such as a Ringer's solution, Hartmann's solution, Saline and/or the like is then introduced into central chamber 302 and/or into peripheral chamber 304, such that the separation-enabling agent covers both the entirety of central chamber 302 and at least a portion of peripheral chamber 304.

Then, semen sample 308 and separation-enabling agent 310 may be left for a period of optionally 15 to 60 minutes in a temperature of optionally 30-37 degrees Celsius, allowing motile cells to swim up through separation-enabling agent 310 and at least partially into peripheral chamber 304. After the specified period, the motile cells may be collected, manually or automatically, from peripheral chamber 304.

Cell separation system 140 may also be operated inversely—a sample may be deposited in peripheral chamber 304 keeping its level below rim 306; a separation-enabling agent may be introduced into central chamber 302 while overflowing rim 306 onto the peripheral chamber; and the components may be left to allow motile cells to swim up from the peripheral chamber into the central chamber.

Generally, a cell separation system such as system 140 or any other system may be constructed according to the principle that a first chamber is adapted to contain a semen sample, and a second chamber is adapted to receive motile cells upon introduction of a separation-enabling agent into the first chamber. In the examples given above, respectively, each of central chamber 302 and peripheral chamber 304 may be the first or the second chamber.

Cell separation system 140 may be used to assess motility of sperm cells of the semen sample, and/or to isolate motile sperm cells of the semen sample for intra uterine insemination (IUI), vaginal insemination and/or in-vitro fertilization (IVF) purposes.

Figure 1B:
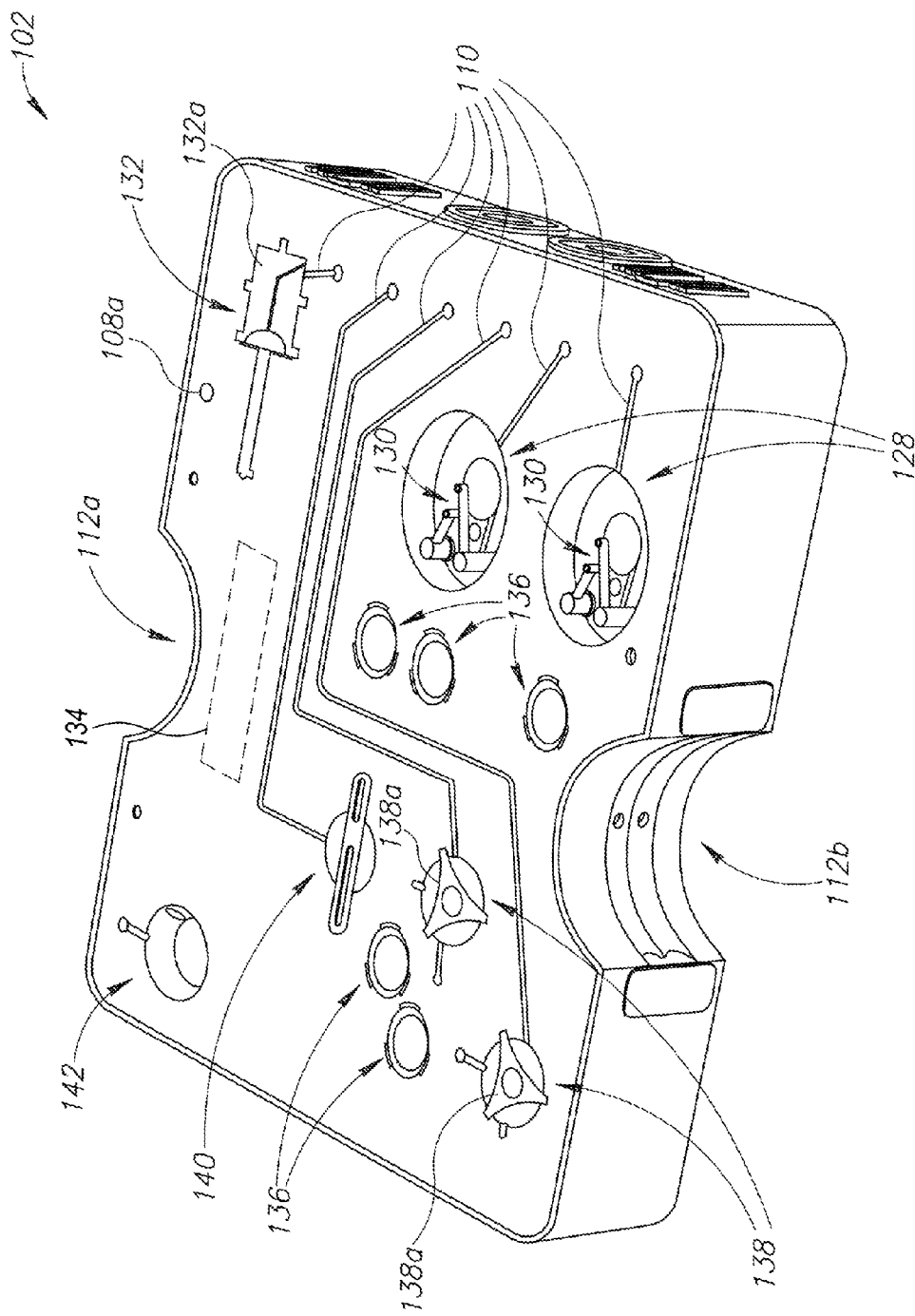
FIG. 1B shows a perspective view of a main body of a sealed, removable cartridge.

Referring now back to FIGS. 1A and 1B, free volume compartment 124 may be adapted to measure and/or to dose the volume or a portion of the volume of the biologic sample. Free volume compartment 124 may be used to hold required dose of the sample and than transfer it to the correct assay, as different assays require different volumes of sample. The volume may be manually read, such as by reading the scale at the sample surface level or by a sensor adapted for such reading.

Figure 1C:
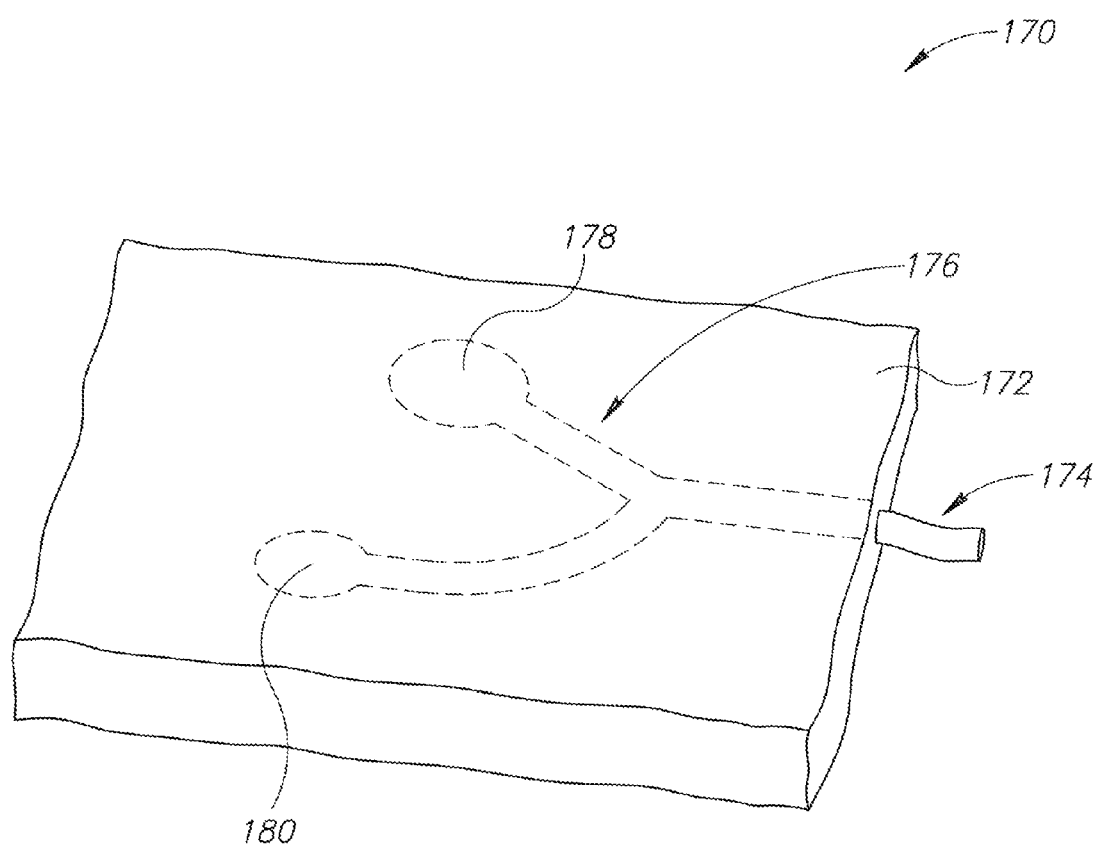
FIG. 1C shows a perspective view of another sealed, removable cartridge.

Reference is now made to FIG. 1C, which shows a perspective view of another exemplary sealed, removable cartridge 170, according to an embodiment. Cartridge 170 may differ from cartridge 100 (FIGS. 1A-B), inter alia, in its essentially flexible housing 172. Flexible housing 172 may be made of any flexible material, such as a polymer, an IV pouch, a food/liquid storage pouch, a hazardous material storage pouch, or any other pouch. Internal conduits 176 may also be flexible, to enable manual or automatic squeezing of housing 172 and the conduits to transport a biologic sample within cartridge 170, towards two or more assay locations such as assay locations 178 and 180.

An Assay Device

Figure 2:
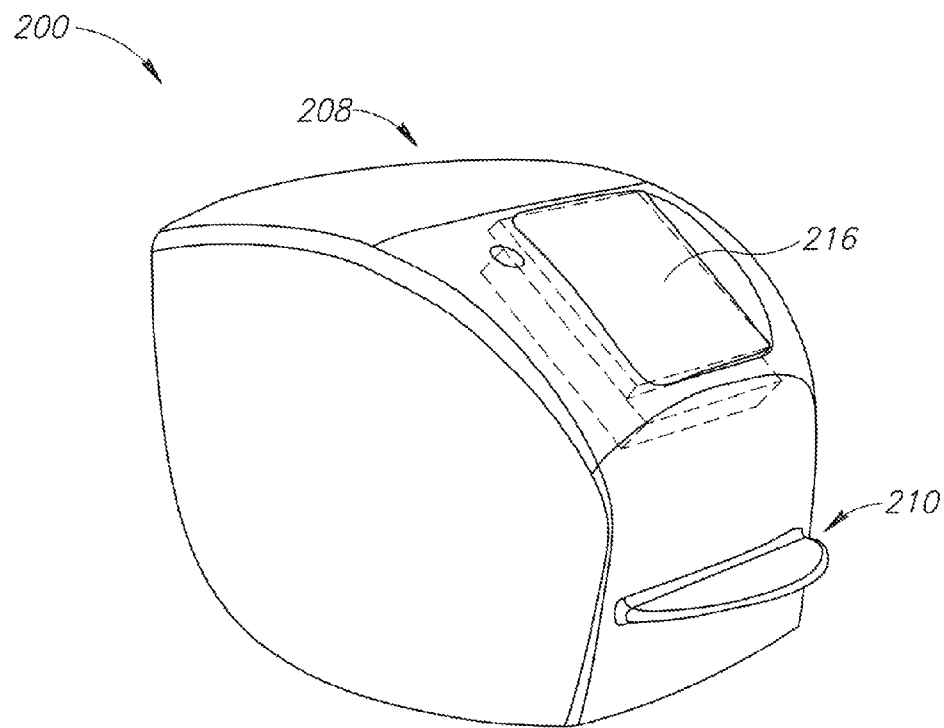
FIG. 2 shows an exploded view of an assay device.
Figure 2:
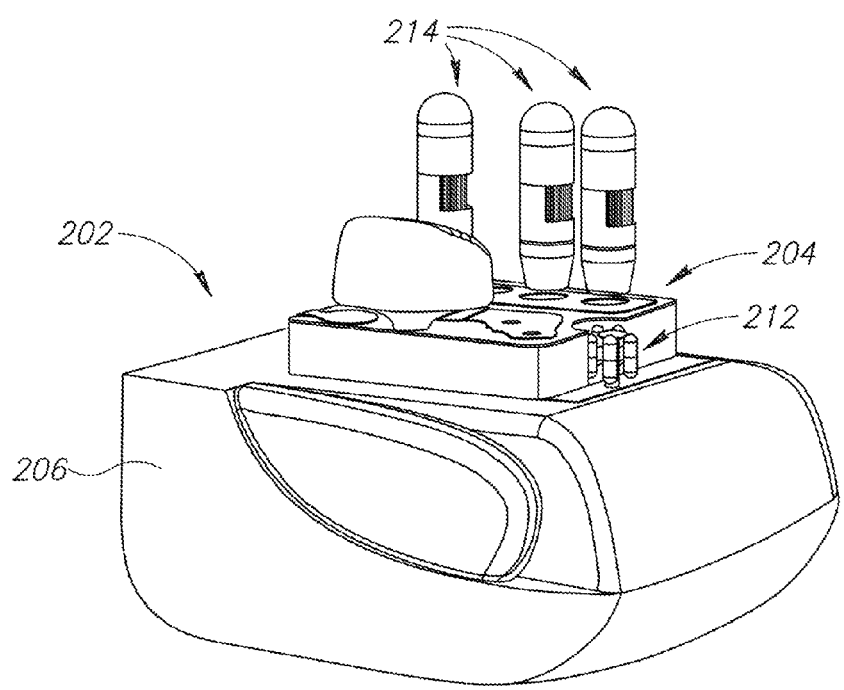

Reference is now made to FIG. 2, which shows an exploded view of an exemplary assay device 200, according to an embodiment. Assay device 200 may include a compartment 202 or any other cavity adapted to receive a cartridge 204, which may be cartridge 100 of FIGS. 1A-B, cartridge 170 of FIG. 1C or any other suitable cartridge. Compartment 202 is shown, for simplicity of presentation, as a space above a base 206 of assay device 200. In other embodiments (not shown), a compartment may be a slot, a recess and/or any other cavity adapted for partial or full insertion of a cartridge.

Assay device 200 may further include a top cover 208 having a handle 210. Top cover 208 may be pivotally connected to base 206, to enable opening of the top cover for insertion and removal of cartridge 204. In other embodiments (not shown), an assay device may structured such that insertion and removal of a cartridge do not necessitate manual opening of a cover, a door or the like. For example, an assay device may include an automatically-opening door or a door which opens upon physical engagement of a cartridge. Alternatively, an assay device may lack a cover or a door at all, so that at least a portion of a cartridge remains exposed when the cartridge is inside its compartment.

Assay device 200 may further include an actuator 212 adapted to interface with cartridge 204 and to provide positive and/or negative gas (such as air or any other suitable gas) pressure to the cartridge. The pressure created by actuator 212 may propagate along one or more conduits within cartridge 204, so that a biologic sample contained in the cartridge is transported along the cartridge. Actuator 212 may be a pump, such as a positive displacement pump, a peristaltic pump or any other type of pump adapted to provide positive and/or negative pressure to the one or more conduits of cartridge 204. Additionally or alternatively, a common syringe or a micropipette, manually or machine operated, may be used.

Additionally or alternatively, a different actuator (not shown) may be at least one roller adapted to squeeze cartridge 204 (or a different cartridge) in order to transport the biologic sample within it.

Assay device 200 may include a means for reading results, or to inspect any other assay within cartridge 100. Results may be read visually, or the device may further include one or more sensors, such as, for example, three sensors 214. At least one of sensors 214 may be adapted to sense one or more parameters pertaining to the biologic sample in cartridge 204, and may be positioned such that it is in sensing stance of at least one assay location of the cartridge.

For example, at least one of sensors 214 may be an image sensor, namely—a camera, adapted to visually inspect at least one assay location of cartridge 204. The image sensor may sense, for instance, a color (via sensed wavelength), a texture and/or the like which exist in the at least one assay ports. The color (via sensed wavelength), a texture and/or shape may be indicative of one or more parameters of the biologic sample. For example, the image sensor may be adapted to sense light at 610-670 nanometers (nm) for detecting apoptosis in the biologic sample. As another example, pH may be read by pH electrode; Turbidity and viscosity sensors may be ones available on the market; a pad loaded with specific reagents also available on the market.

Assay device 200 may further include a processor 216, adapted to control at least one of sensors 214 and/or to process data received from the sensors. Processor 216 may be realized as any available micro processor, micro controller and/or general purpose computer. For example, processor 216 may display locally to its user results of one or more assays performed in cartridge 204. The results may be stored for further processing, displayed in a remote location and/or transferred using communication protocols known in the industry, wired or wireless. As another example, if the biologic sample is a semen sample, processor 216 may analyze a series of temporally-distinct semen samples of the same person, and provide the user with a prediction of an optimal date in which the person's semen may be best for fertilization. That is, processor 216 may recognize a pattern of gradually changing fertility factors (such as sperm cell concentration, sperm cell motility and/or the like) and calculate, accordingly, future fertility factors in that same tested person. When conducting an assay of female factors, for example, estrogen and progesterone profiles, it may be possible to predict a date in which fertilization is in its best. Combining both predictions yields a better chance for successful fertilization, and an "optimal fertilization date" may be jointly determined.

Processor 216 may be further adapted to perform one or more of facilitating at least one of the assays, receiving a reading from the at least one sensor, computing a result of at least one of the assays, and/or computing a combined measure of results of two or more of the assays, hence concluding different results. Such a combined measure may be used as a fertility index. As an example, male subjects with low sperm qualities may get a higher index score by changing their way of life, avoiding oxidative stress or other methods known in prior art.

Reference is now made to FIG. 4, which shows a perspective view of another assay device 400, according to an embodiment. Assay device 400 may be relatively easy to operate and its operation may require no special laboratory training, so that a nurse, a physician, or any other caregiver may operate it in what is often referred to as a "point of care"—a clinic, a medical institution or the like. Furthermore, the assay device may still be operated in a laboratory.

Assay device 400 may include a compartment 402 adapted to receive a receptacle, such as a condom or a sample collecting cup, containing a reproduction system sample such as semen, vaginal secretions, cervical mucus, vaginally-collected cells and/or the like. Optionally, the receptacle is the one disclosed in applicant's PCT Published Application No. WO 2008/035333.

Figure 4A:
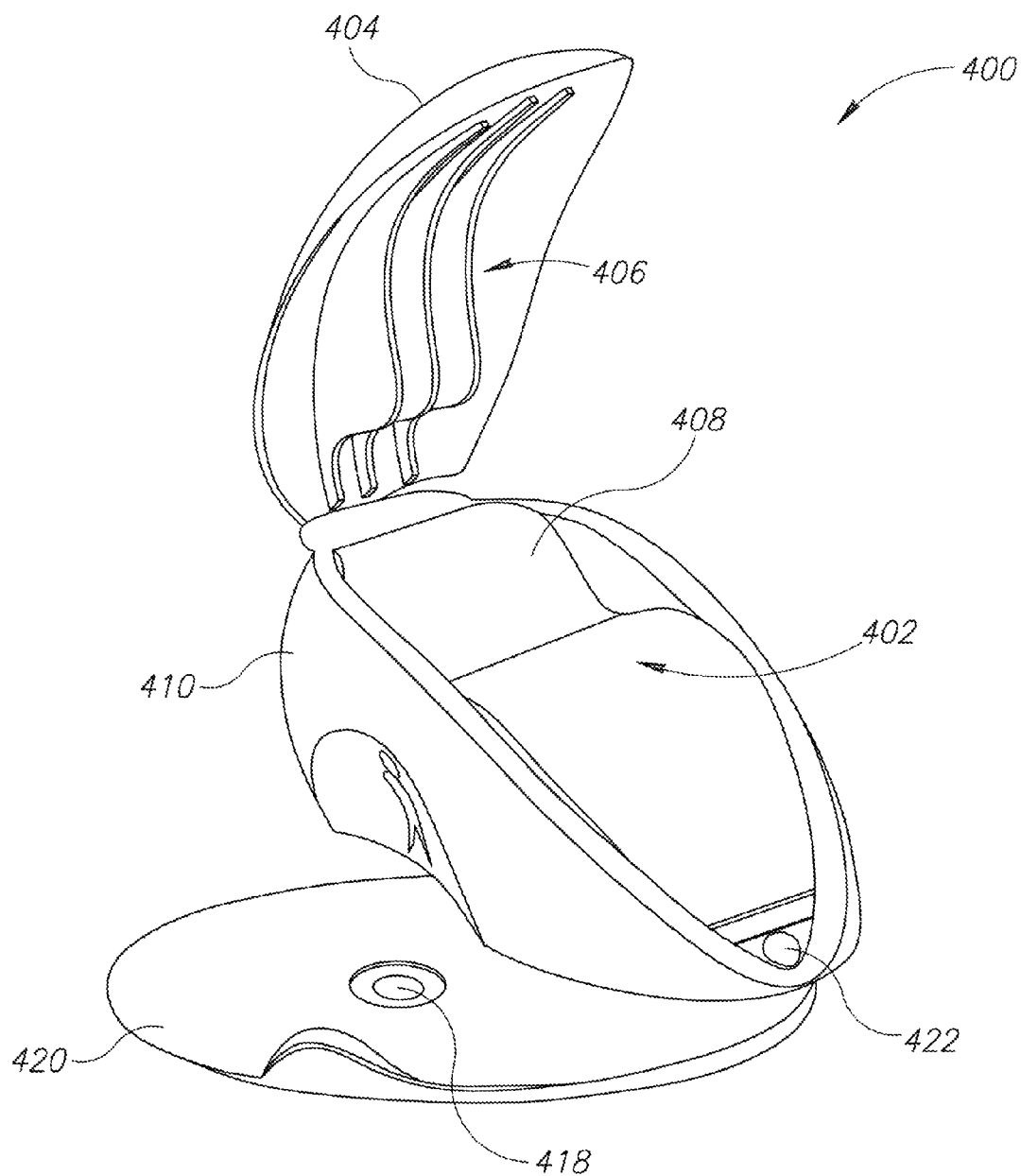
FIG. 4A shows a perspective view of an assay device.
Figure 4B:
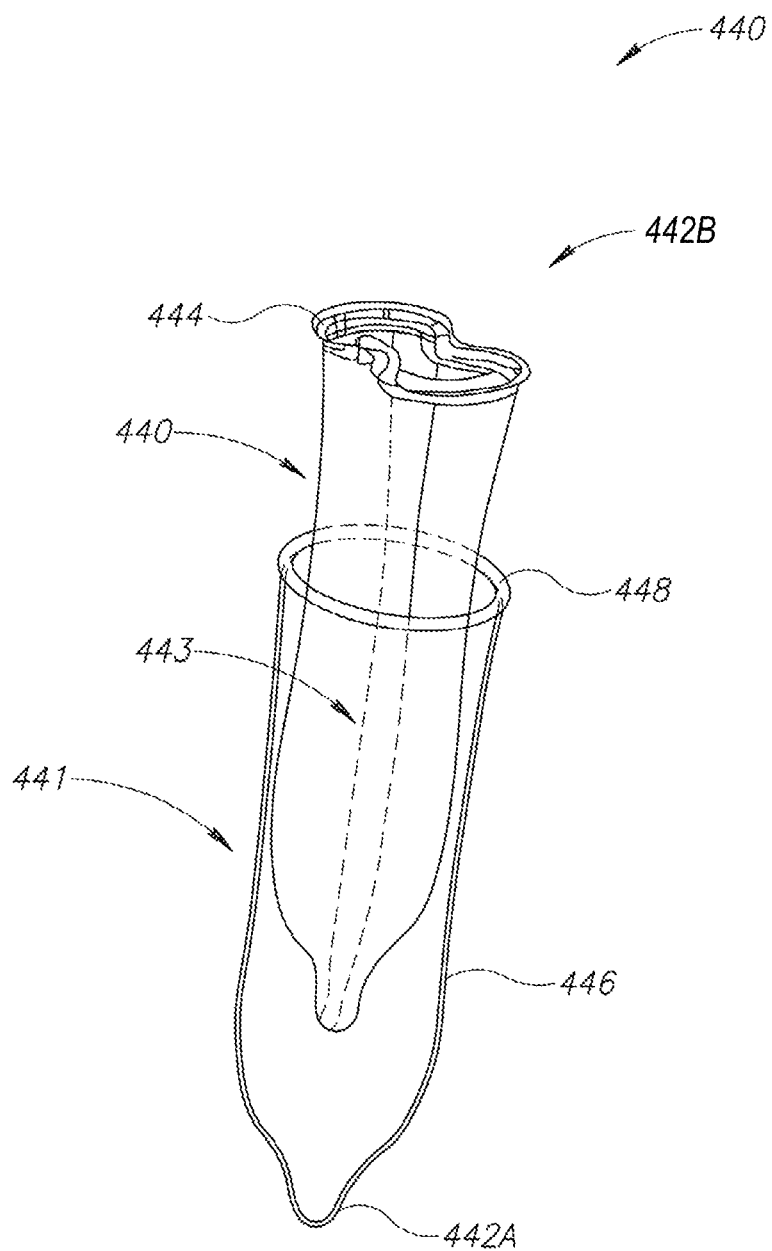
FIG. 4B shows a perspective view of a receptacle.

Referring now to FIG. 4B, an exemplary receptacle 440 is shown. Receptacle 440 may include an elongated, flexible bag, which may have a condom-like shape with inner cavity (such as 443) defined by the walls of the receptacle bag (440). The narrow end 442A of the receptacle may be at least partially sealed. For example, the walls at the narrow end of the receptacle may exhibit pore sizes of less then 0.42 nm. The broad end 442B, which is distally opposing the narrow end 442A, may be open. The broad, open end 442B may further include a rim 444 that may be used for the association of the receptacle within a contraceptive, as detailed below herein. Rim 444 is illustrated at a deformed state, wherein the rim is shaped into an eight form, by, for example, pinching two opposing sides of the rim towards each other. The receptacle 440 may be constructed of rubber, silk, polyurethane, silicone and the like. The thickness of the receptacle may vary in the range of about 5 to 1500 microns. Size of receptacle 140 may vary in length and diameter. For example, length of receptacle 440 from end 442A to end 442B may be in the range of, about 100-200 mm. For example, diameter of rim 444 of receptacle 440 may be in the range of, about 37 to 60 millimeter. Receptacle (such as 440) may further be associated with a male contraceptive device, such as a condom 446. Receptacle 440 may be fitted into male condom 446, such that the receptacle is contained within the inner space of the condom. Shown in FIG. 4B is a receptacle 440 fitted about two thirds of its length into a condom 446. Receptacle 440 may be secured to condom 446 by various ways. For example, rim 444 and rim 448 of condom 446 may be associated by pressing, stitching, mechanical fitting, zip-lock fit, zipper fit, fitting grooves, adhering, gluing and the like. For example, rim 444 of receptacle 440 may include perforation/grooves that may be used to fit to the upper rim, 448 of condom 446.

Reference is now made back to FIG. 4A. Assay device 400 may include an extraction mechanism for extracting the reproduction system sample from the receptacle and for transporting the reproduction system sample towards one or more assay ports and/or treatment ports, where the reproduction system sample is assessed and/or treated, respectively.

The extraction mechanism may be embodied as a strike handle 404 pivotally attached to a main body 410 of assay device 400, and having a protruding structure 406 matching a structure of a recess 408 in the main body. The receptacle may be positioned in compartment 402 with its reproduction system sample-containing edge at recess 408, and handle 404 may be lowered so as to squeeze the receptacle and extract at least some of its reproduction system contents.

Alternatively, the extraction mechanism may include a peristaltic pump (not shown) and/or a set of rollers adapted to induce the reproduction system sample out of the receptacle. Alternatively, the extraction mechanism may be the receptacle itself, being elastic in nature and therefore manually squeezable by a user.

Figure 4C:
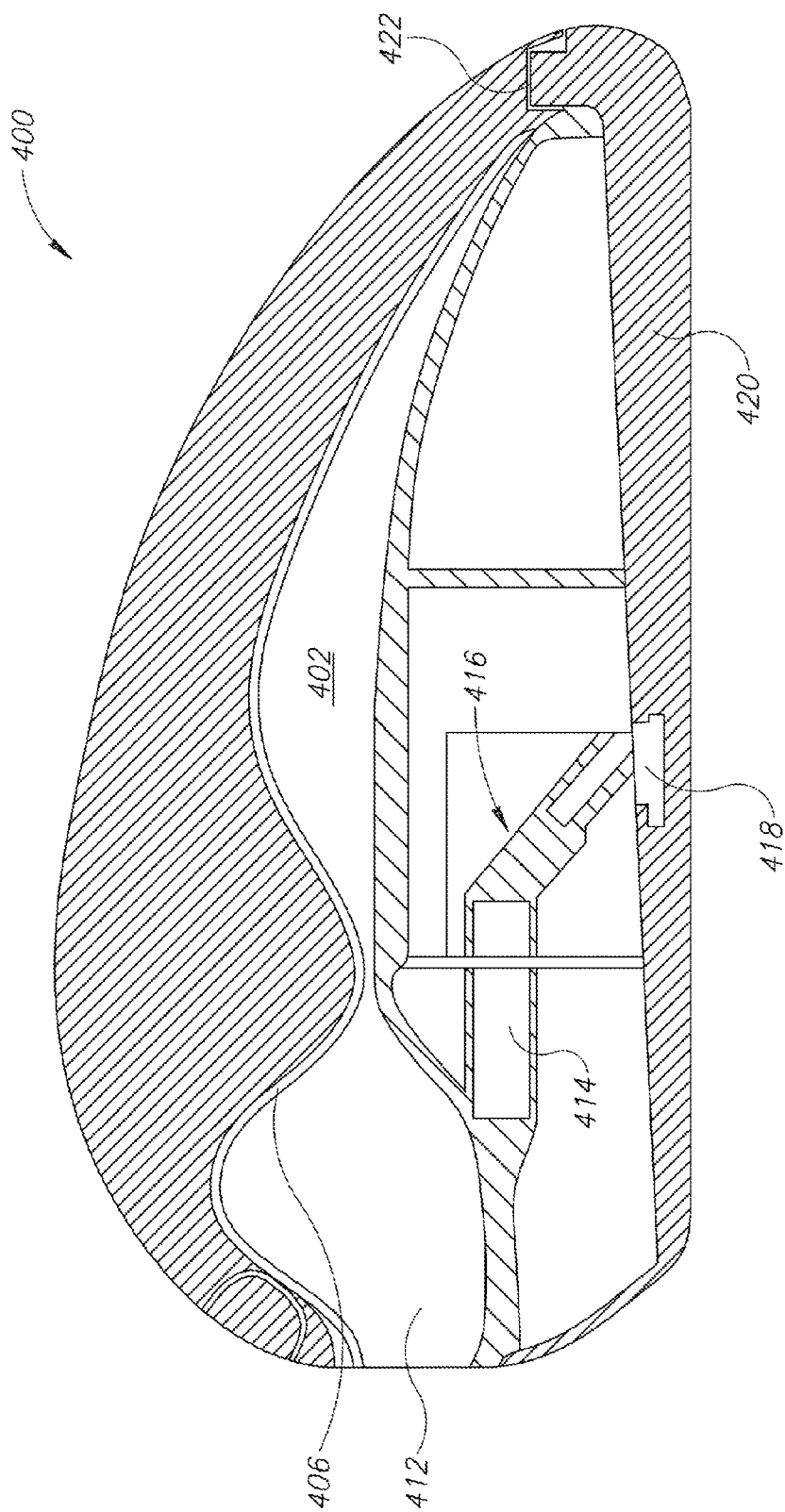
FIG. 4C shows a cross-sectional view of an assay device.

Reference is now made to FIG. 4C, which shows a cross-sectional view of assay device 400. Before, during or after extraction of the receptacle's reproduction system contents, the volume of the reproduction system is optionally measured in a chamber 412.

The extracted reproduction system may be forced, by virtue of the extraction mechanism, to a conduit 414 leading to one or more assay locations, such as assay location 416. The one or more assays are optionally those described above in regard to cartridge 100 (FIGS. 1A-B).

When the one or more assays are complete, at least one chemical may flow to a result indicator such as a color-changeable result pad 418, causing the pad to change color responsive to the assay result. Result pad 418 may be embedded in a sliding base 420 of assay device, and the sliding base may be pivotally attached, using a hinge 422, to main body 410. Sliding base 420 may be slid by the user when the one or more assays are complete, to reveal result pad 418 and see the result.

Handle 404, or any other part of assay device 400, may include a reference color scale (not shown) for comparing the shade, shape, texture and/or the like of result pad 418 to a reference and thus providing the user with a meaningful result. The reference color scale may be printed on handle 404 or attached to it as a sticker. The reference color scale optionally includes literal explanation of the meaning of each color; the explanation may, additionally or alternatively, be included in product literature accompanying assay device 400.

Optionally, assay location 416 is a replaceable, and is adapted to be replaced by an additional assay location for facilitating an additional assay. This way, assay device 400 may be used multiple types for performing the same assay (such as an assay pertaining to fertilization potential which may have to be repeated every once in a while) or may be used each time for performing a different assay of the same semen sample or a different semen sample.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A device for assaying at least one biological sample, comprising:
    a. at least one removable cartridge, adapted to facilitate one or more assays of said at least one biological sample, said cartridge comprising a body, said body comprises:
        i. at least one compartment adapted to contain said at least one biological sample;
        ii. one or more assay locations, in which at least one of said assays of said at least one biological sample is provided; and
    b. at least one actuator adapted to interface with said cartridge to enable transportation of said at least one biological sample towards at least one of said assay locations,
    wherein said compartment comprises:
        i. a central chamber shaped as an open dimple in said body, said central chamber is bounded by a first rim defining a perimeter of said central chamber; and
        ii. a peripheral chamber shaped as an open circumferential depression extending entirely around said central chamber, said peripheral chamber is shallower than said central chamber and is bounded by said first rim and a second outer rim which extends higher than said first rim, such that upon introduction of a separation-enabling fluid, said portion of said at least one biological sample can be separated according to its relative motility by transfer from one of said central chamber and said second peripheral chamber to the other over said first rim at any point along said perimeter of said central chamber.

2. The device according to claim 1, wherein said removable cartridge is sealed such that no contamination of the environment outside said cartridge is enabled.

3. The device according to claim 1, further comprising a reagent that, upon contact with said biological sample, reacts and/or produces a colored compound, said reagent selected from the group consisting of: cell support medium, labeling compounds, markers, peptide, color-changeable pad and any combination thereof.

4. The device according to claim 1, wherein said biological sample is selected from the group consisting of: a semen sample, a vaginal secretion sample, a vaginal cell sample, a blood sample, a urine sample, a saliva sample, a lymph sample and any combination thereof.

5. The device according to claim 1, wherein said assay is selected from the group consisting of: a sperm concentration assay, a semen pH assay, a leukocyte threshold assay, a sperm motility assay, a sperm morphology assay, a semen volume assay, a viscosity assay, and a turbidity assay; further wherein said assay is adapted to facilitate diagnosis of at least one sexually transmitted disease (STD) selected from the group consisting of: syphilis, gonorrhea, Candida infection, human papilloma virus (HPV) infection, mycoplasma, ureaplasma, human immunodeficiency virus (HIV) infection, Chlamydia infection, herpes simplex virus infection, Hepatitis B, Trichomonas infection, and Hepatitis C.

6. The device according to claim 1, wherein said cartridge is made of substantially rigid materials or a substantially flexible materials or any combination thereof.

7. The device according to claim 1, wherein said actuator comprises a pump, a peristaltic pump, means of pressure difference creation, strike handle, a set of rollers, manual activation selected from a pipette, micropipette injector, syringe, any positive displacement or any combination thereof.

8. The device according to claim 1, further comprising a controller programmed to perform at least one action selected from a group consisting of: (i) receive a reading from said at least one sensor, said sensor is in communication with said cartridge; (ii) analyze said reading; (iii) analyze readings received based upon said at least one of said assays; and (iv) output said analysis of said biological sample.

9. The device according to claim 1, wherein said cartridge is further adapted to facilitate a cell separation assay; said cell separation assay is adapted to assess motility of sperm cells and/or isolate or separate motile sperm within a semen sample for assisting fertility.

10. The device according to claim 9, wherein said rim is configured with specific surface roughness or serration to facilitate required surface tension capabilities for specific sample/reagent combination.

11. The device according to claim 9, wherein said cell separation system is adapted to isolate motile sperm cells of said semen sample for a use selected from the group consisting of: intra uterine insemination (IUI), vaginal insemination, and in-vitro fertilization (IVF) and diagnosis of motile sperm cell.

12. The device according to claim 9, wherein said separation-enabling agent is selected from the group consisting of Ringer's solution, Hartmann's solution, Saline, cell support medium, cell washing medium, preparation medium, and any separation-enabling agent adapted to facilitate said separation of said sperm cells from said semen sample.

13. The device according to claim 1, wherein said cartridge is further adapted to manipulate said biological sample using at least one manipulation technique selected from the group consisting of: homogenization, liquefaction, deposition on a reagent-loaded pad, mixing with a reagent, deposition on an antibody-loaded pad, incubation, separation, migration and sedimentation, and swim-up.

14. The device according to claim 1, wherein said at least one assay location comprises two or more assay locations.

15. A method for assaying at least one biological sample, comprising acts of:
    a. providing a device according to claim 1; and
    b. operating said device by steps of:
        i. inserting at least one biological sample into said at least one compartment within said body of said removable cartridge;
        ii. operating said actuator, thereby transporting said at least one biological sample to said central chamber while keeping said biological sample's level below said first rim; and
        iii. introducing a separation-enabling fluid into at least one of said central chamber and said second peripheral chamber, such that said separation-enabling fluid covering the entirety of said central chamber and at least a portion of said peripheral chamber; thereby motile cells swim up through said separation-enabling fluid into said peripheral chamber.

16. The method according to claim 15, further comprising providing said removable cartridge sealed such that no contamination of the environment outside said cartridge is enabled.

17. The method according to claim 15, further comprising contacting a reagent with said biological sample, wherein said reagent is selected from the group consisting of cell support medium, labeling compounds, markers, peptide, color-changeable pad or any combination thereof.

18. The method according to claim 17, further comprising at least one step selected from the group consisting of (a) providing said at least one assay locations with two or more assay locations; and (b) providing said at least one assay comprising two or more assays.

19. The method according to claim 17, further comprising selecting said separation-enabling agent from the group consisting of Ringer's solution, Hartmann's solution, Saline, cell support medium, cell washing medium, preparation medium and any separation-enabling agent adapted to facilitate said separation of said sperm cells from said semen sample.

20. The method according to claim 15, further additionally comprising at least one step selected from:
selecting said biological sample from the group consisting of: a semen sample, a vaginal secretion sample, a vaginal cell sample, a blood sample, a urine sample, a saliva sample and a lymph sample or any combination thereof; and
selecting said assay from the group consisting of: a sperm concentration assay, a semen pH assay, a leukocyte threshold assay, a sperm motility assay, a sperm morphology assay and a semen volume assay, a viscosity assay and a turbidity assay.

21. The method according to claim 20, additionally comprising assessing motility of sperm cells and/or isolating motile sperm within a semen sample for assisting fertility, by said cell separation assay.

22. The method according to claim 15, further comprising acilitating diagnosis of at least one sexually transmitted disease (STD) selected from the group consisting of: syphilis, gonorrhea, Candida infection, human papiloma virus (HPV) infection, mycoplasma, ureaplasma, human immunodeficiency virus (HIV) infection, Chlamydia infection, herpes simplex virus infection, Hepatitis B, Trichomonas infection, and Hepatitis C by said assay.

23. The method according to claim 15, further comprising selecting said actuator from the group consisting of a pump, a peristaltic pump, means of pressure difference creation, strike handle, a set of rollers, manual activation selected from a pipette, micropipette injector, syringe, any positive displacement and any combination thereof.

24. The method according to claim 15, further comprising at least one step selected from the group consisting of:
receiving a reading from at least one sensor, said sensor is in communication with said cartridge;
analyzing said reading;
analyzing readings received based upon said at least one of said assays; and
outputting said analysis of said biological sample via control means.

25. The method according to claim 15, additionally comprising manipulating said biological sample using at least one manipulation technique selected from the group consisting of: homogenization, liquefaction, deposition on a reagent-loaded pad, mixing with a reagent, deposition on an antibody-loaded pad, incubation, separation, migration and sedimentation and swim up by said cartridge.

* * * * *

UNITED STATES PATENT AND TRADEMARK OFFICE
CERTIFICATE OF CORRECTION

| | | |
|---|---|---|
| PATENT NO. | : 9,168,028 B2 | Page 1 of 1 |
| APPLICATION NO. | : 12/739337 | |
| DATED | : October 27, 2015 | |
| INVENTOR(S) | : Vered Shany et al. | |

It is certified that error appears in the above-identified patent and that said Letters Patent is hereby corrected as shown below:

On the title page item (54) and in the specification column 1, line 1, should read:

BIOLOGICAL SAMPLE ASSAY DEVICE

Signed and Sealed this
Twenty-ninth Day of March, 2016

Michelle K. Lee
*Director of the United States Patent and Trademark Office*